(12) United States Patent
Siwy et al.

(10) Patent No.: US 7,708,871 B2
(45) Date of Patent: May 4, 2010

(54) NANODEVICE FOR CONTROLLED CHARGED PARTICLE FLOW AND METHOD FOR PRODUCING SAME

(75) Inventors: Zuzanna Siwy, Darmstadt (DE); Jan Behrends, Munich (DE); Niels Fertig, Munich (DE); Andrzej Fulinski, Cracow (PL); Charles R Martin, Gainesville, FL (US); Reinhard Neumann, Dossenheim (DE); Christina Trautmann, Darmstadt (DE); Eugenia Toimil Molares, Darmstadt (DE)

(73) Assignee: Gesellschaft fuer Schwerionenforschung mbH, Darmstadt (DE)

( * ) Notice: Subject to any disclaimer, the term of this patent is extended or adjusted under 35 U.S.C. 154(b) by 1216 days.

(21) Appl. No.: 10/528,520

(22) PCT Filed: Sep. 24, 2003

(86) PCT No.: PCT/EP03/10631

§ 371 (c)(1),
(2), (4) Date: Nov. 4, 2005

(87) PCT Pub. No.: WO2004/028673

PCT Pub. Date: Apr. 8, 2004

(65) Prior Publication Data

US 2006/0163071 A1 Jul. 27, 2006

(30) Foreign Application Priority Data

Sep. 25, 2002 (DE) ................. 102 44 914

(51) Int. Cl.
*G01N 27/447* (2006.01)
*G01N 27/453* (2006.01)
(52) U.S. Cl. .................... 204/450; 204/600
(58) Field of Classification Search ......... 204/450–455, 204/600–605
See application file for complete search history.

(56) References Cited

U.S. PATENT DOCUMENTS 5,593,560 A 1/1997 Inoue .............. 210/644

(Continued)

FOREIGN PATENT DOCUMENTS

DE 198 53 286 A 5/2000

(Continued)

*Primary Examiner*—Alex Noguerola
(74) *Attorney, Agent, or Firm*—Frommer Lawrence & Haug LLP; Ronald R. Santucci

(57) ABSTRACT

The present invention relates to an apparatus having a nanodevice (1) for controlling the flow of charged particles in an electrolyte. Such apparatus comprises an electrolytic bath container (2) divided by a polymeric membrane foil (3) into a first (4) and a second compartment (5), wherein each compartment (4, 5) comprises an electrode (6, 7) connected to a voltage supply (8). Further the apparatus comprises at least one asymmetric pore (9) forming a via hole through said foil (3), wherein said pore (9) provides a narrow opening (10) of a diameter in the range of several nanometers down to about one nanometer on a front side (11) of said foil (3) and a wide opening (12) in the range of several ten nanometers up to several hundred nanometers on a back side (13) of said foil (3). Further, the apparatus comprises an electrically conductive layer (14) surrounding said narrow opening (10) on said front side (11) and a gate voltage supply (15) connected to said electrically conductive layer (14) on said front side (11) of said foil (3) controlling the flow of charged particles within said nanodevice (1) from said first compartment (4) to said second compartment (5) vice versa. The invention further relates to a method for producing such a nanodevice (1).

25 Claims, 3 Drawing Sheets

U.S. PATENT DOCUMENTS

| | | | |
|---|---|---|---|
| 5,736,050 A | 4/1998 | Pasternak et al. | 204/671 |
| 6,627,067 B1 * | 9/2003 | Branton et al. | 205/778 |
| 7,077,939 B1 * | 7/2006 | Crooks et al. | 204/450 |

FOREIGN PATENT DOCUMENTS

| | | |
|---|---|---|
| JP | 53 091079 A | 8/1978 |
| JP | 62 186904 A | 8/1987 |
| WO | WO 02/20877 A | 3/2002 |
| WO | WO 02/36230 A | 5/2002 |

* cited by examiner

1) $U_2 = 0$     $I$

2) $U_2 > 0$     $I - \Delta I$

3) $U_2 < 0$     $I + \Delta I$

NANODEVICE FOR CONTROLLED CHARGED PARTICLE FLOW AND METHOD FOR PRODUCING SAME

This is a 371 filing of International Patent Application No. PCT/EP2003/010631 filed Sep. 24, 2003 and published on Apr. 8, 2004 under publication number WO 2004/028673 A and claims priority benefits from German Patent Application No. 102 44 914.7 filed Sep. 25, 2002 and U.S. patent application Ser. No. 10/254,947 filed Sep. 25, 2002.

The present invention relates to a apparatus having a nanodevice for controlling the flow of charged particles in electrolytes and method for producing same.

In many electrolytic systems the problem of controlling ion flow, rather than flow of electrons, is crucial. For the flow of electrons diodes and transistors are the basic elements controlling, switching on and off and amplifying the signal. For the ionic current there exist very limited possibilities to tune the ion flow. From German patent application 100 44 565.9 an electrochemical rectifier is known, based on preparation of asymmetric pores in a polymeric foil. One mode of operation entails applying a constant voltage across a membrane with asymmetric pores, however changing the current would require changing the concentration and/or the pH-value of the electrolyte. Since this changing of concentration and/or pH-value is time consuming and disturbs the condition of operation, this option may not be applicable for a given system.

Therefore, it is the object of the present invention to provide an independent "switch", which would be able to modulate the ion current through the pore with a minimum disturbance of the operation conditions. Further, it is an object of the present invention to control the transport of charged or ionized large molecules.

According to the invention an apparatus having a nanodevice for controlling the flow of charged particles in electrolytes is provided, comprising an electrolytic bath container, divided by a polymeric foil into a first and a second compartment. Each compartment comprises an electrode connected to a voltage supply. Further, the nanodevice comprises at least one preferentially asymmetric pore forming a via hole through said foil, wherein said pore provides a narrow opening of a diameter in the range of several nanometers down to about one nanometer on a front side of said foil and a wide opening in the range of several ten nanometers up to several hundred nanometers on a back side of said foil.

The polymeric foil is covered on its front side by an electrically conductive layer surrounding said narrow opening. A gate voltage supply is connected to said electrically conductive layer on said front side of said foil controlling the flow of charged particle within said nanodevice from said first compartment to said second compartment and vice versa.

This nanodevice has the advantage to control or to switch on and off a charged particle flow of heavy ions, ions of macromolecules, ions of bio-molecules, ionized dimeric, ionized oligomeric or ionized polymeric DNA or ionized insulin. In such a nanodevice with such a pore the spatial distribution of electric potential inside the pore is changed by the gate voltage on the electrically conductive layer of the polymeric foil in order to advantageously tune the flow of ion through the pore. The electrically conductive layer forms a gate close to the narrow opening of the conical, funnel-like, or trumpet-like pore or at the entrance of a cylindrical pore, where the pore has its highest resistance. Such a gating ion flow would allow to control ionic current through the asymmetric pore.

In a preferred embodiment the polymeric foil comprises polyethylene terephthalate, polyimide or polycarbonate. These materials have the advantage, that an ion trace can be performed through said foil by a high accelerated ion like bismuth. Such a trace across a foil material can be etched in an electrolytic cell consisting of two cell halves filled with an electrolytic solution and being divided by said foil comprising said ion trace. These materials have further the advantage that a nanodevice made of same is cation selective.

Another preferred embodiment comprises a gold layer as electrically conductive layer surrounding said narrow opening of said front side. Such a gold layer as a gate electrode has the advantage, that it is resistive against corrosion and oxidation. Therefore, such gold layer can be used in different electrolytic bathes to control and/or switch on an off a flow of charged particles.

Another preferred material for the gate electrode is a semiconductor like indium oxide or ITO. Indium oxide has the advantage, that it is erosion and oxidation resistant in almost any electrolytic bath.

In a further preferred embodiment the back side of said foil is covered by an electrically conductive layer surrounding said wide opening. Such a second metal layer on the back side of the polymeric foil enables the nanodevice to make the ion current changes finer and better controlled.

The nanodevice is not limited either to polymer films or to a gold layer, since any asymmetric and charged nanopores together with a conductive layer, which can be charged by a voltage, can be potentially used to accomplish the present invention.

A membrane with asymmetric pores enables an optimal control of the particle flow, offering at the same time higher mass flow than a corresponding cylindrical pore of the same effective diameter. The principles of functioning of the nanodevice are valid however also for symmetric, for example, cylindrical pores with a metal (or semiconductor) layer sputtered on one side of the membrane. This broadens immensely the possibilities of manufacturing a device of this kind, because also commercially available membranes with cylindrical pores of any material (e.g. polymer, anodic alumina) can be used. By applying voltage to the layer, it makes the system asymmetric as far as distribution of electric potential inside the pore is concerned.

Covering the conductive layer by a thin insulating layer that is chemically inactive in an electrolyte solution limits the influence of the "gate" potential to the entrance of the pore with said layer. This is expected to improve the control over the charged particle flow.

Ion flow control is possible also with pores of diameter up to hundreds of nm. In said large-pore set-up the layer representing the third electrode is preferentially made of a non-insulating i.e. electrically conductive material. The pores are not selective with respect to different ion species, and the mechanism of ion flow control differs from that in very narrow pores. The potential on the conductive layer ($U_2$) superimposes the potential difference applied across the membrane ($U_1$), which for given voltage configurations provides the possibility of enhancing or stopping anions (cations). This was demonstrated with a membrane containing $10^7$ pores/$cm^2$ and methylene blue dye.

One preferred mode of operation of the nanodevice is to provide a direct current voltage supply for the electrolytic bath and a direct current voltage supply for the gate voltage. Another preferred mode of operation is to apply an alternating voltage to the gate, which enables to achieve a pulse-like flow of charged molecules through said nanodevice with at least one asymmetric pore.

Preferred applications of the apparatus having a nanodevice are
1. Separation processes for the pharmaceutical industry,
2. Controlled release of bio-molecules like insulin,
3. Voltage-controlled nanosystems,
4. Tuning of the ion current signal,
5. Gating of ionic bio-molecule in microfluid lab-on-a-chip devices.

The invention is further related to a method for producing a nanodevice. Such a method comprises the steps of:
  irradiating a membrane of a polymeric foil by at least one high accelerated ion to form an ion trace through said foil;
  etching said ion trace from a back side of said foil toward a front side of said foil to form a pore having a wide opening on said back side in the range several ten nanometers up to several hundred nanometers and a narrow opening on said front side in the range of several nanometers down to about one nanometer;
  drying said etched foil;
  depositing an electrically conductive layer on said front side by diminishing the narrow opening;
  reopen said narrow opening to a predetermined diameter by etching said conductive layer from its back side.

This method has the advantage that a conical, a funnel-like or a trumpet-like nanopore is performed along the ion trace through the polymeric foil dependent on the parameters of an electrolytic process in an electrolytic cell consisting of two cell halves filled with an electrolytic solution.

In a preferred method at least a single bismuth ion is accelerated to an energy in the range of 10 to 15 MeV and irradiated toward said polymeric foil to form said ion trace. This bismuth ion is particularly advantageous if applied to foils made of polyethylene terephthalate, polyimide and/or polycarbonate. This trace is preferably etched by a caustic solution, where such a caustic solution can comprise 9 m NaOH. This caustic solution has the advantage that the ion trace can be etched at room temperature. After etching along the ion trace an asymmetric pore, the front side of the foil is deposited with a electrically conductive layer like a gold or indium oxide layer by a sputter technique.

To increase the adhesiveness of an electrically conductive layer like a gold layer or a semiconductor layer on the polymer surface of the foil, it is an advantage to roughened the surface of the polymer foil before etching the irradiated film.

During said deposition of a metal or a semiconductor on said front side the narrow opening is diminished. To reopen said narrow opening a piece of a conductive tape is attached to cover the conductive layer. After that it is an advantage to reinsert said foil with its electrically conductive layer and said piece of a conductive tape in an electrolytic cell, wherein the two cell halves are filled with potassium fluoride, whilst a conductive tape stays attached to the conductive layer.

Further embodiments, features and advantages of the invention are now discussed with reference to the attached drawings.

FIG. 5$a,b$ show examples of time series without and with applied "gate voltage" for two directions of the potassium ion flow.

Figure 1:
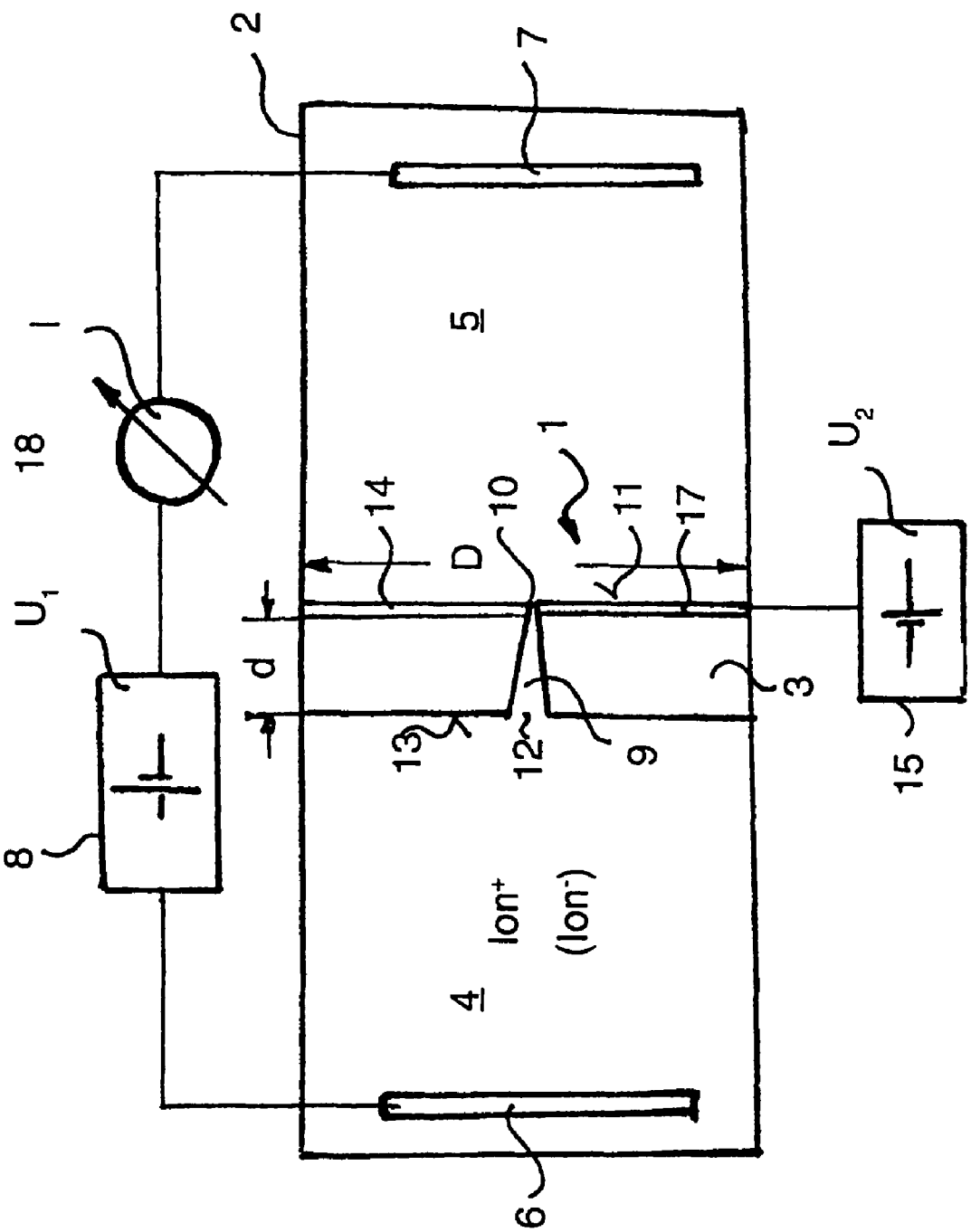
FIG. 1 shows a schematic drawing of an apparatus having a nanodevice for controlling the flow of charged particles in electrolytes.

FIG. 1 shows an embodiment of an apparatus having a nanodevice 1 for controlling the flow of charged particles (ion$^+$ or ion$^-$) in an electrolyte. This apparatus comprises an electrolytic bath container 2 divided by a polymeric foil 3 into a first 4 and a second 5 compartment. Each compartment 4 and 5 comprises an electrode 6 and 7 connected to a voltage supply 8, which supplies in this embodiment a direct current voltage $U_1$. The electrolytic current I is measured by a current meter 18.

If the potential of electrode 6 is positive, positive charged particles like ion$^+$ are forced through the asymmetric pore 9 of the foil 3 from a wide opening 12 on the back side 13 of the foil 3 to a narrow or small opening 10 on the front side of said foil 3. The foil itself is a circular disc having a diameter D of about 30 mm and a thickness d of 12 μm. The material of the foil in this embodiment is polyethylene terephthalate which was irradiated in its center with a single bismuth ion of 11.4 MeV specific energy and etched from one side in a 9 m NaOH at room temperature to form said pore 9.

The polymeric foil 3 is covered on the front side 11 by a gold layer surrounding the narrow opening 10 of said pore 9. This gold layer functions as a gate electrode 17, which is supplied by a gate voltage $U_2$ supply 15. If this gate voltage $U_2$ is negative, the charged particles in the first compartment 4 like ion$^+$ are accelerated, so that the flow through the nanodevice 1 is increased toward the second compartment 5. When Increasing $U_2$ toward a positive gate voltage the flow of positive charged particles (ion$^+$) is decreased and can even be switched off.

Figure 2:
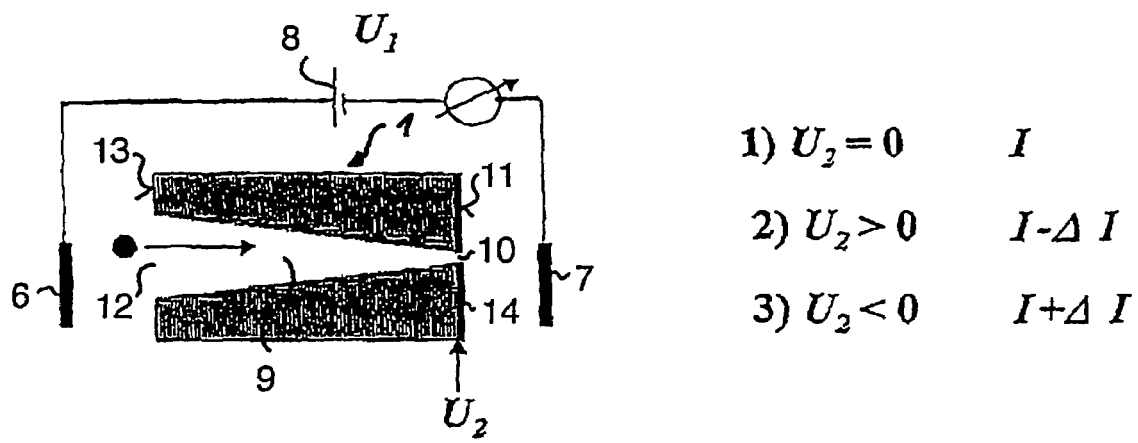
FIG. 2 shows principles of the functioning of the nanodevice for controlling the flow of charged particles in electrolytes.

FIG. 2 shows principles of the functioning of the nanodevice 1 for controlling the flow of charged particles (ion$^+$, ion$^-$) in electrolytes. Components with the same functions as in FIG. 1 are characterized by the same reference signs and an explanation of same is omitted.

FIG. 2 shows in detail the principles of operating a device shown in FIG. 1. A thin layer 14 of metal or semiconductor is sputtered on the front side 11 of the foil 3 having such narrow openings 10. This layer 14 can be charged via an independent electric circuit $U_2$. If the pore is very narrow, the passage of the ions through the pore will be influenced by such a "gate". The pore produced by a track-etching technique in a foil 3 made of polyethylene terephthalate, polyimide or polycarbonate are negatively charged due to formation of carboxylate groups, therefore they are cation-selective. This means that cations are the main charge carriers.

Applying a positive voltage $U_2$ slows down the flow of cations observed as lower current. Applying a negative voltage $U_2$ has an opposite effect, the current will be larger. Accordingly, this device will be the first device, which can control the ion flow, based on asymmetry of electric potential introduced by the conical, funnel-like or trumpet-like shape of a charged nanopore in combination with applying locally electric fields. Since this layer can be charged positively or negatively by means of the voltage applied via an independent circuit, this results in changes of the profile of the electric potential at the pore constriction, which influences the ion current flow.

Figure 3:
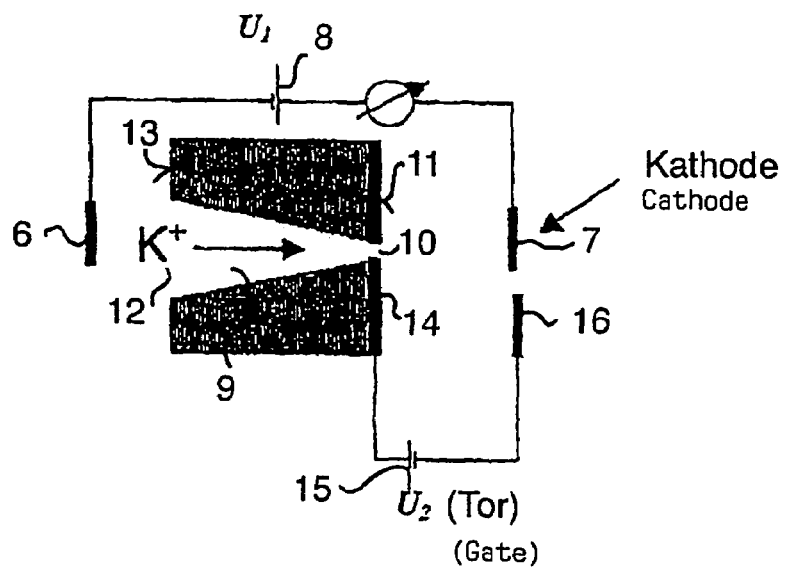
FIG. 3 shows a scheme of an experimental set-up for evaluating the performance of the nanodevice.

FIG. 3 shows a scheme of an experimental set-up of evaluating the performance of the nanodevice 1. Components having the same functions as in FIG. 1 or in FIG. 2 are characterized by the same reference signs and an explanation of same is omitted.

The evaluation of the performance of the nanodevice 1 is made for a single pore within a 12 μm thick circular disc of 30 mm diameter. For the purpose of etching such a pore in a 9 m NaOH this disc or membrane is inserted between two halves of an electrolytic cell and sealed hermetically by applying pressure onto the two cell halves. When the etching process is completed, the polymer foil 3 is removed from the cell and dried. In a next step, a gold layer 14 is sputtered on the front side 11 with its narrow opening 10. Then, a piece of a conductive tape is attached to the front side onto the gold layer. Now, the foil is inserted back into the electrolytic cell, which chambers are now filled with potassium fluoride.

The current through the pore 9 is measured with electrodes of Ag/AgCl. An independent circuit is built, which applies a voltage to the gold layer via the conductive tape. The scheme of the experimental set-up is shown in FIG. 3. The use of fluoride ions in a KF solution increases the effect of the applied voltage during the electrolytic procedure. $F^-$ ions do not adsorb to the gold layer.

Figure 4:
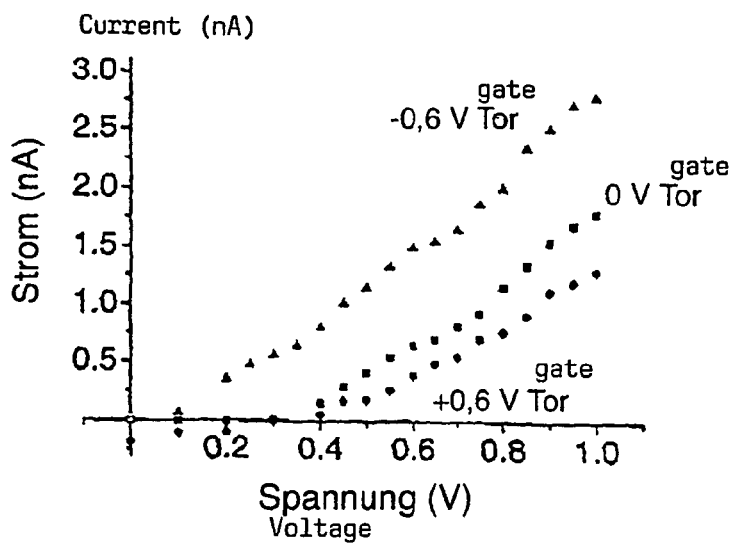
FIG. 4 shows current-voltage characteristics of a single conical pore in a polyethylene terephthalate (PET) foil with a gold layer on the side of the small or narrow opening of a pore, applying 0.1 m KF on both sides of the membrane foil.

FIG. 4 shows a current-voltage characteristic of a single conical pore 9 in a PET-foil. The abscissa of said diagram shows the voltage $U_1$ in V and the ordinate shows the current in nA. The dotted curves shows the effect of the parameters: +0.6 V at the metal gate electrode, 0V at the metal gate and −0.6 V at the metal gate. As one can see from this evaluation it is possible to enhance the current through the asymmetric pore at a voltage $U_1$ of 0.4 V by a gate voltage $U_2$ of −0.6 V up to around 1 nA, whilst with a positive gate voltage of 0.6 V the ionic current is decreased to 0 or shut off.

Figure 5A:
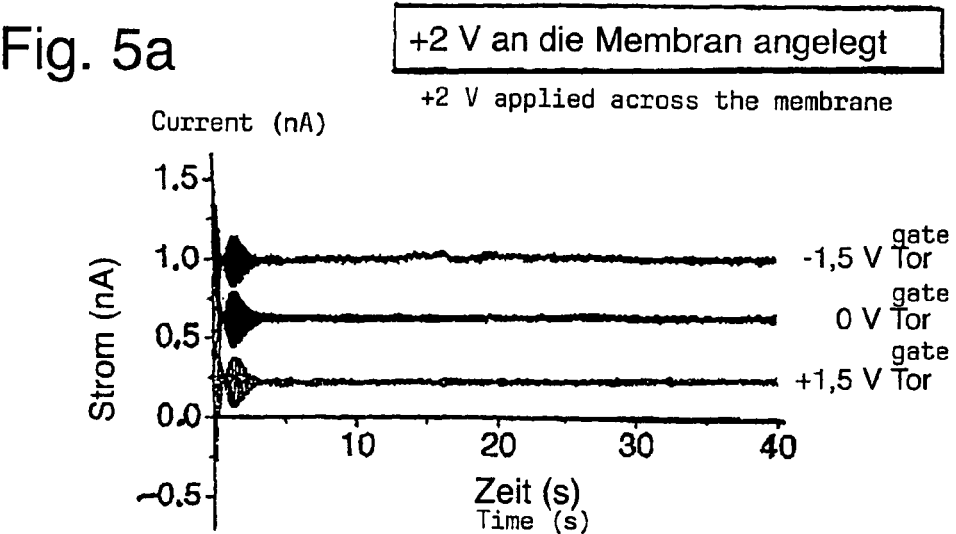
Figure 5B:
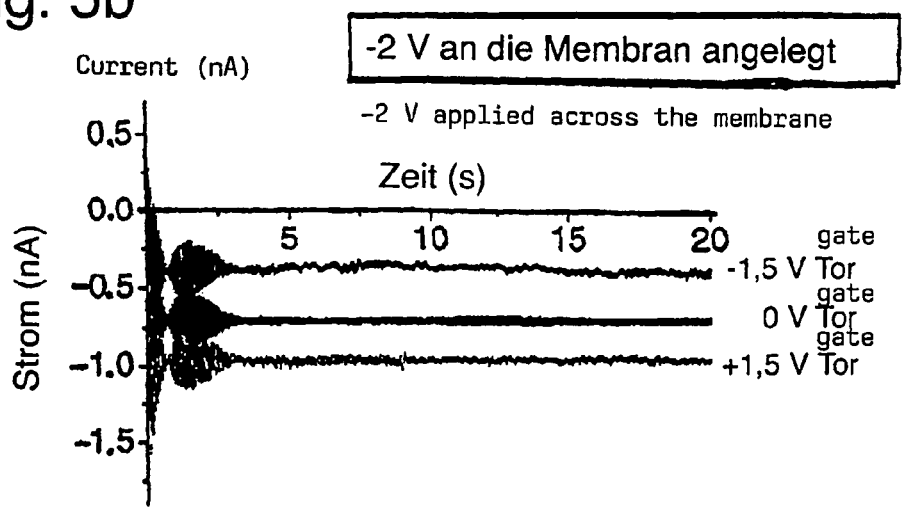

FIGS. 5a and 5b show examples of time series without and with applying a gate voltage for two directions of the potassium ion flow. If a voltage of +2V is applied across the membrane a voltage of +1.5V at the gate will decrease the current drastically, whilst a gate voltage of −1.5 will increase the current up to 1 nA. In these diagrams of FIGS. 5a and 5b the abscissa shows the time in seconds and one can see that after three seconds the current is relatively constant.

In FIG. 5b the voltage across the membrane or across the pore is changed to −2V, so that the current is also negative. By applying negative gate voltage of about −1.5V the current is decreased, whilst applying a positive gate voltage of 1.5V the current is increased to −1 nA. This diagrams show that this nanodevice is quite sensitive and works like a triode for ions in an electrolytic bath.

LIST OF REFERENCE SIGNS

1 nanodevice
2 electrolytic bath container
3 polymeric foil
4 first compartment
5 second compartment
6 electrode
7 electrode
8 voltage ($U_1$) supply
9 asymmetric pore
10 narrow opening
11 front side
12 wide opening
13 back side
14 electrically conductive layer
15 gate voltage ($U_2$) supply
16 electrode
17 gate electrode
18 current meter

The invention claimed is:

1. An apparatus comprising:
   a nanodevice for controlling the flow of charged particles, wherein the nanodevice comprises a polymeric foil and at least one preferentially asymmetric pore forming a via hole through said foil, wherein said pore provides a narrow opening of a diameter in the range of several nanometers down to about one nanometer on a front side of said foil and a wide opening in the range of several ten nanometers up to several hundred nanometers on a back side of said foil, and wherein an electrically conductive layer surrounds said narrow opening on said front side;
   an electrolytic bath container that is divided by said polymeric foil into a first and a second compartment, wherein each of the first and second compartment comprises an electrode connected to a direct current voltage ($U_1$) supply; and
   a gate voltage ($U_2$) supply connected to said electrically conductive layer on said front side of said foil controlling the flow of charged particles within said nanodevice from said first compartment to said second compartment and vice versa.

2. The apparatus according to claim 1, wherein said preferentially asymmetric pore is a preferentially conical pore.

3. The apparatus according to claim 1, wherein said preferentially asymmetric pore is a funnel-like pore from said wide opening toward said narrow opening.

4. The apparatus according to claim 1, wherein said asymmetric pore is a straight trumpet-like pore from said narrow opening toward said wide opening.

5. The apparatus according to claim 1, wherein said foil comprises polyethylene terephthalate.

6. The apparatus according to claim 1, wherein said foil comprises any polymer, preferentially polyimide.

7. The apparatus according to claim 1, wherein said foil comprises polycarbonate.

8. The apparatus according to claim 1, wherein said nanodevice is ion selective.

9. The apparatus according to claim 1, wherein said electrically conductive layer surrounding said narrow opening on said front side comprises gold.

10. The apparatus according to claim 1, wherein said electrically conductive layer surrounding said narrow opening on said front side comprises indium oxide.

11. The apparatus according to claim 1, wherein said electrically conductive layer surrounding said narrow opening on said front side is a gate electrode.

12. The apparatus according to claim 1, wherein said back side of said foil is covered by an electrically conductive layer surrounding said wide opening.

13. The apparatus according to claim 1, wherein said nanodevice is applied to control or to switch on and off a charged particle flow of heavy ions, ions of macromolecules, ions of bio-molecules, ionized dimeric, ionized oligomeric or ionized polymeric DNA or ionized insulin.

14. A method for producing a nanodevice of an apparatus according to claim 1 comprising the steps of:
   irradiating a membrane of a polymeric foil by at least one highly accelerated ion to form an ion trace through said foil;
   etching said ion trace;
   drying said etched foil;
   depositing an electrically conductive layer on said front side by diminishing the narrow opening;
   reopen said narrow opening to a predetermined diameter by etching said conductive layer from its back side.

15. The method according to claim 14, wherein a single bismuth ion is accelerated to an energy in the range of 10 to 15 MeV and irradiated toward said polymeric foil to form said ion trace.

16. The method according to claim 14, wherein said ion trace is etched by a caustic solution.

17. The method according to claim 16, wherein said caustic solution comprises 9 m NaOH.

18. The method according to claim 14, wherein said ion trace is etched at room temperature.

19. The method according to claim 14, wherein said deposition is carried out by sputtering a metal or a semiconductor on to said front side (11).

20. The method according to claim 14, wherein said front side (11) of said foil (3) is roughened before etching said ion trace.

21. The method according to claim 14, wherein said membrane is inserted in an electrolytic cell consisting of two cell halves filled with a KF solution and being divided by said membrane and sealed hermetically to etch said ion trace.

22. The method according to claim 14, wherein a conductive tape is attached to the conductive layer before said reopening of said narrow opening is performed.

23. The method according to claim 22, wherein said foil covered on its front side by a conductive tape is reentered to said electrolytic cell, which cell halves are now filled with NaF.

24. A method to control an ion flow with pores of a diameter up to hundreds of nm within a membrane, which constitute a large-pore set-up, the method comprising:
providing, within said large-pore set-up, a layer representing a third electrode of an electrically conductive material, wherein the pores are not selective with respect to different ion species; and
superimposing, using the potential on the conductive layer ($U_2$), a potential difference applied across the membrane ($U_1$), which for a given voltage configuration enhances or stops ions.

25. The method of claim 24, wherein the membrane contains $10^7$ pores/cm$^2$ and is made of a methylene blue dye.

* * * * *